(12) United States Patent
Goldberg et al.

(10) Patent No.: US 6,268,368 B1
(45) Date of Patent: Jul. 31, 2001

(54) ANIONIC EXCHANGE POLYMER COMPLEXES OF BUSPIRONE

(75) Inventors: Arthur H. Goldberg, Menlo Park, CA (US); Ahmed Adel Sakr, Cincinnati, OH (US)

(73) Assignee: American Pharmaceuticals International, Cincinnati, OH (US)

( * ) Notice: Subject to any disclaimer, the term of this patent is extended or adjusted under 35 U.S.C. 154(b) by 0 days.

(21) Appl. No.: 09/516,232

(22) Filed: Mar. 1, 2000

(51) Int. Cl.⁷ .................................................. A61K 31/495
(52) U.S. Cl. ..................................... 514/252.15; 424/78.15
(58) Field of Search ..................... 424/78.15; 514/252.15

(56) References Cited

U.S. PATENT DOCUMENTS 5,431,922 * 7/1995 Nicklasson .......................... 424/490
5,980,882 * 11/1999 Eichman ........................... 424/78.12

* cited by examiner

*Primary Examiner*—Frederick Krass
(74) *Attorney, Agent, or Firm*—Philip M. French

(57) ABSTRACT

A controlled release form of buspirone medicament is described. This medicament comprises a buspirone in intimate admixture with an anionic exchange polymer complexing agent. These components form a complex upon the addition of water and thereby permit improved dosing of buspirone to achieve a more targeted therapeutic effect in patients.

15 Claims, 3 Drawing Sheets

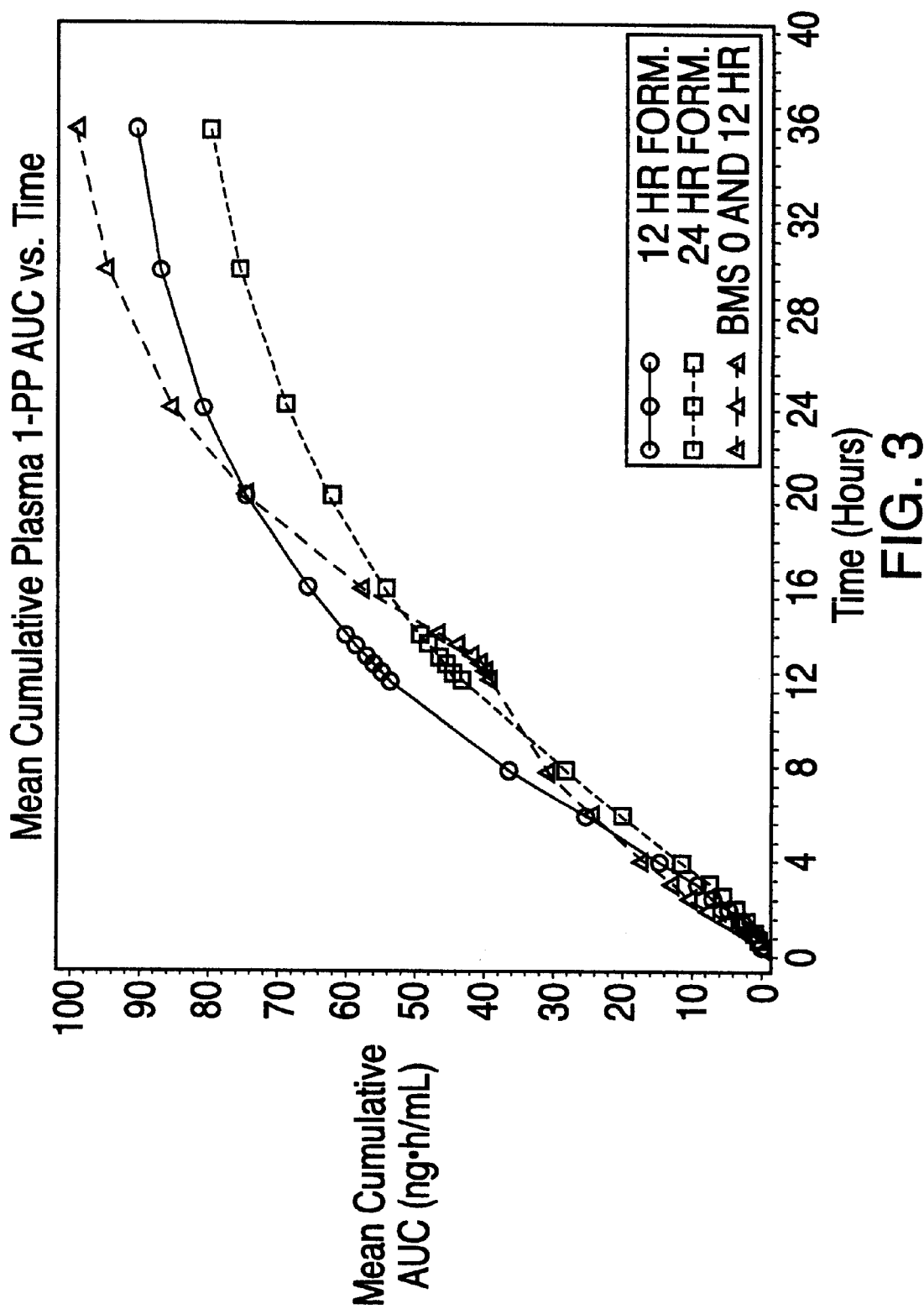

ANIONIC EXCHANGE POLYMER COMPLEXES OF BUSPIRONE

FIELD OF THE INVENTION

This invention relates broadly to buspirone and improved means for dosing patients to achieve a desired therapeutic effect with a complex of buspirone and anionic exchange polymer.

BACKGROUND OF THE INVENTION

Buspirone, chemically: 8-4-4-2-pyrimidinyl)-piperazinyl [butyl]-8-azaspiro(4,5)-decane-7, 9-dione is a pharmaceutically active compound disclosed in U.S. Pat. No. 3,717,634. This compound has been found to be effective for the treatment of anxiety disorders including depression.

Buspirone suffers from the drawback of a very high first pass metabolism. Only about 4% of a therapeutic dose will ordinarily reach the systemic circulation unchanged after oral administration (Mayol et al., Clin. Pharmacol. Ther., 37, 210, 1985).

Buspirone also exhibits great intra- and inter-individual variations in absorption. This variability has been demonstrated by up to 10-fold differences in the maximum plasma concentrations resultant from a given dose of this drug (Gammans et al., American J. Med., 80, Suppl. 3B, 41–51, 1986).

Several metabolites of buspirone have been identified, including several hydroxylated derivatives that show little pharmacological activity. The major metabolite, 1-(2-pyrimidinyl piperazine (1-PP), has been found to be about 20–25% as potent an anxiolytic agent as buspirone in pharmacologic testing.

The biological half-life of buspirone is very short and variable in man, on an order of 2–11 hours. The much less active metabolite, 1-PP, exhibits much slower elimination (Mayol et al., Clin. Pharmacol. Ther., 37, 210 1985). These pharmacokinetic properties necessitate a rather frequent daily dosing regimen which would be expected to have a negative effect on patient compliance.

Since buspirone is rapidly absorbed after an oral dose, high peak plasma values normally occur shortly after drug administration. These peak values are associated with the occurrence of undesired or adverse events commonly observed during the first days of treatment. These adverse effects can also seriously impact patient compliance because they can result in deliberate disruption of the drug therapy.

Since its clinical introduction, buspirone has suffered from a perceived lack of immediate effect. Much of this perception may be attributable to patient failures in compliance. Patient monitoring has evidenced inappropriate dosing—either using buspirone as a night-time dose or taking it as necessary (prn)—instead of using it in the consistent manner in which it is ordinarily prescribed.

Wide variation and unpredictability in the delivery of buspirone have been reported in articles such as Metabolism and Disposition of Buspirone by Gammans et al, the *American Journal of Medicine*, Mar. 31, 1988, Vol. 80. These studies reflect that systemic availability and plasma levels of buspirone may differ by 1,000% or more, dependant on the individual and other factors.

Attempts to improve the oral delivery of buspirone have been only partially successful. U.S. Pat. No. 5,431,922 describes formulations of buspirone or a salt thereof imbedded in an inert matrix; formed into micro pellets; and in coated micro pellets to obtain an intermediate in vitro dissolution rate. This intermediate dissolution rate is said to permit less frequent dosing and reduced production of 1-(2-pyrimidinyl-2-piperazine (1-PP) metabolite. However, the comparative data in the examples of that patent continue to reflect wide variation in the buspirone plasma concentration levels, both over time and between patients.

SUMMARY OF THE INVENTION

This invention concerns an improved oral dosage formulation for the controlled release of buspirone medicament. This formulation comprises an intimate admixture of buspirone or a pharmaceutically acceptable salt thereof with an anionic exchange polymer complexing agent. The desired complex of these components is ordinarily formed in situ on contact with water incident administration of the formulation. Alternatively, the component can be pre-complexed in water and then administered to a patient.

Solid forms of these buspirone and anionic exchange polymer components may be incorporated into pills, tablets, capsules, pellets or micro pellets using any convenient carrier agents. These dosage forms preferably include a viscosity enhancing or gelling agent such as hydroxypropylmethyl cellulose.

These medicament tablets or other solid forms comprising buspirone or a pharmaceutically accepted addition salt thereof with an anionic exchange polymer may be orally administered in an anxiolytically effective dose to an anxious individual for the palliative treatment of anxiety neurosis.

In addition to facilitating the controlled release of buspirone, the present complexes moderate the pharmacokinetics of this drug. This results in dramatic mitigation of the common variations in individual reception of buspirone. Therefore the buspirone-ion exchange polymer complexes of the present invention permit enhanced targeting of therapeutic amounts and effects of this drug.

BRIEF DESCRIPTION OF DRAWINGS

The invention and the Examples will be more clearly understood when considered with the accompanying drawings in which:

FIG. 3 is a graphic depiction of the comparative results obtained for mean cumulative plasma levels of 1-(2-pyrimidinyl)-piperazine metabolite in Example 3.

DETAILED DESCRIPTION OF THE INVENTION

Figure 1:
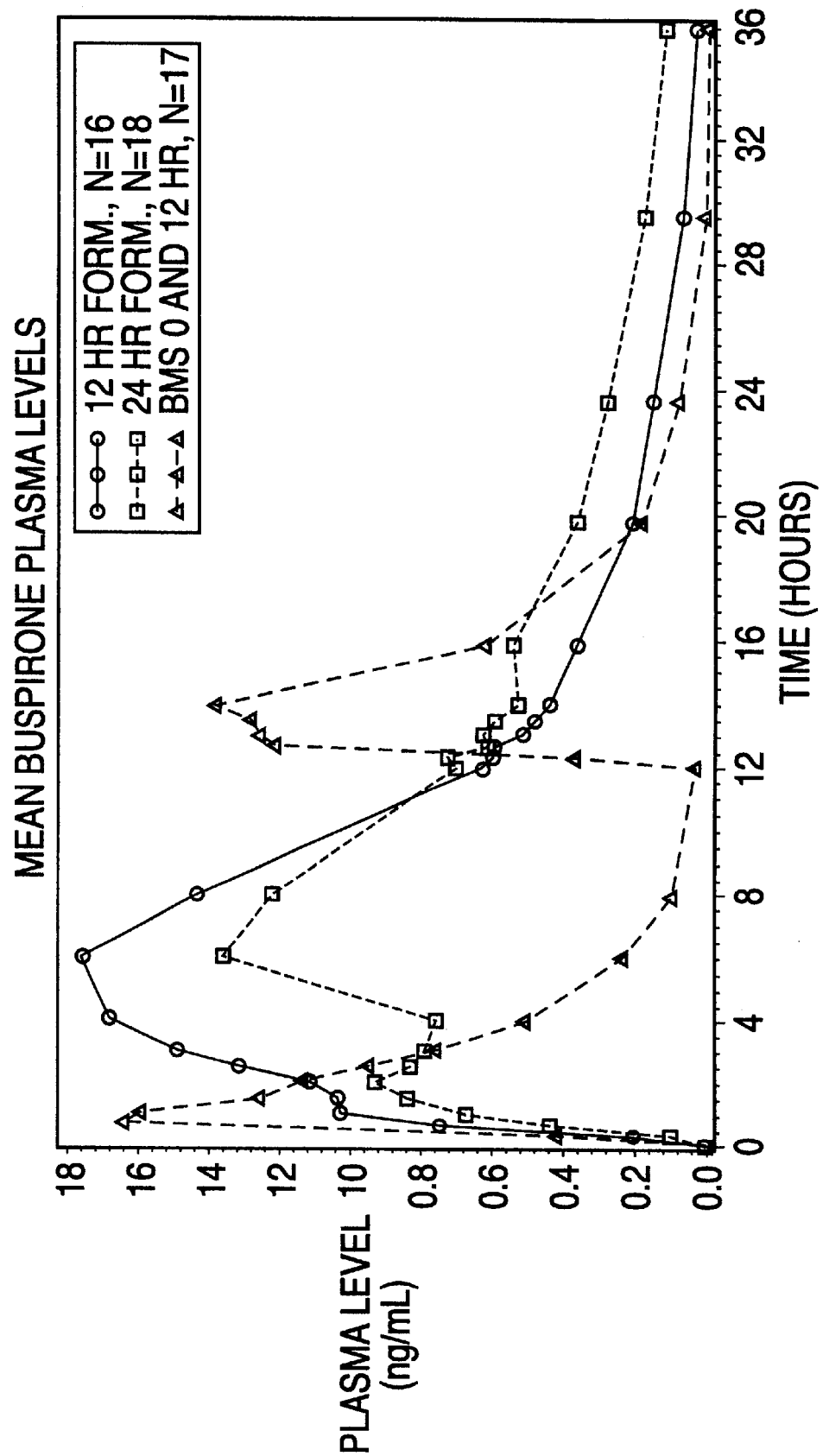
FIG. 1 is a graphic depiction of the comparative results obtained for mean buspirone plasma levels in Example 3.

It has been found that prolonged or sustained release of buspirone, under the conditions encountered in the gastrointestinal tract, may be achieved through an oral dose of medicament in which the buspirone is or becomes bound in situ as a complex with an anionic exchange polymer.

The buspirone employed to form this complex may be in any conventional form. Most commonly, it is provided as an acid addition salt, preferably buspirone hydrochloride, because of the acceptance of that salt for pharmaceutical purposes.

The anionic exchange polymer with which the buspirone is complexed may also vary widely. The selection of an optimum polymer depends upon the form of the buspirone component and may be made in accordance with well known parameters to facilitate complex formation. Especially preferred anionic exchange resins are sodium carboxymethylcellulose and methacrylic acid/ethylacrylate copolymer. Both complex readily with buspirone hydrochloride.

The nature of the ion exchange polymer can also vary widely within the scope of this invention. To facilitate the controlled release of buspirone, it is desirable that the polymer be hydrophilic. Preferably it is also readily dispersable in the aqueous environment of the gastrointestinal tract and therefore has an average molecular weight of less than 500,000.

The buspirone and ion exchange polymer are complexed in conventional manner. Normally, solid powders of these two components, with or without optional additives, are simply admixed. The complex forms upon exposure to water, either in preparing a liquid dosage form or in situ when a solid dosage form comes in contact with the aqueous fluids of the gastrointestinal tract.

The medicament complex of buspirone-ion exchange polymer may be combined with a wide variety of pharmaceutically acceptable components, conventional in the art, to provide a suitable dosage formulation. For example, where the present medicament is provided in solid tablet form, the complex may be combined with conventional dispersant and tableting agents. These include pharmaceutically acceptable dispersants, fillers, flow agents and/or lubricants.

In a preferred embodiment of the present invention, the medicament and complexing agent are additionally combined with a conventional viscosity enhancer or gelling agent. Most desirably, this component is a hydrophilic polymer such as hydroxylmethylcellulose or polyvinyl pyrolidone. Such a gelling agent appears to insulate the buspirone from the in vivo environment of the gastrointestinal tract, facilitating the absorption of the buspirone into the blood stream.

Normally the daily dosage form of this medicament contains less than about 100 mg, desirably between 10 and 60 mg, more desirably between 15 and 40 mg buspirone. The weight ratio of buspirone to anionic exchange polymer may likewise vary widely. Normally, however, this ratio is between 4:1 and 1:6, desirably between 3:1 and 1:4 and more desirably between about 2:1 and 1:4.

The complexes of the present invention substantially prolong the release of buspirone, as compared to conventional in vitro dissolution times for this drug. Such times are measured by means of the USP paddle method at 50 and/or 100 rpm. In accordance with this method, the complexes of this invention have a dissolution time in water which is in excess of 24 hours for about 50 to 75% by weight of buspirone. By way of comparison, dissolution times for commercially available buspirone in un-complexed form normally exceed 80% in 30 minutes, while the form of buspirone in U.S. Pat. No. , 5,431,922 is described as a releasing at least 80% of its buspirone in from 6 to 24 hours. These differences emphasize the degree to which release of this drug is extended by the anionic exchange polymer complex of the present invention.

The following examples are not intended to limit the present invention, but are merely illustrative thereof. It is understood that one of ordinary skill in the art would be able to make substitutions, change proportions, or make other variations, all within the scope of the teachings and without departing from the spirit of this invention, without undue experimentation.

EXAMPLE I

A series of six 20 ml aqueous test solutions of 0.05 mM buspirone hydrochloride were prepared. Five of the solutions were admixed respectively with 0.04, 0.08, 0.12, 0.16 and 0.20 ml aqueous solutions of 5 mM Eudragit L 100-55. Eudragit L 100-55 is an anionic copolymer of methacrylic acid and ethyl acrylate having an average molecular weight of 250,000 and a free carboxyl to ester group ratio of approximately 1:1. Eudragit polymers are commercially available from Rohm, a company of the Huls Group. 1 M NaOH and/or water was then added to bring each test solution and a 20 ml blank solution of the Eudragit to a total volume of 21 ml and a pH of 7.2.

All seven solutions were then measured for UV adsorption at a wave length of 250 nM. This corresponds to a buspirone peak at which Eudragit exhibits no masking absorption.

A plot of the six buspirone and buspirone-Eudragit solutions showed a linear decline in absorbence with increasing concentrations of Eudragit. Calculation from the plot yielded a bonding constant of about 30,000, indicating the strong complex formed between buspirone and this anionic exchange polymer.

EXAMPLE II

The procedure of Example I was repeated substituting a 5 mM solution of sodium carboxymethylcellulose. A plot of the seven solutions again showed a linear decline in absorbence. The plot reflected a bonding constant of about 670,000, indicating a very strong complex between the buspirone and this anionic exchange polymer.

EXAMPLE III

Tablets of buspirone and anionic exchange polymer were prepared as follows:

TABLE I

| Formulations | 24 Hour mg Tablet | 12 Hour mg/Tablet |
|---|---|---|
| Buspirone HCl | 30.0 | 30.0 |
| Hydroxymethylcellulose, High Viscosity | 58.0 | — |
| Hydroxymethylcellulose, Low Viscosity | 0.0 | 60.0 |
| Eudragit L 100-55 | 40.0 | 26.0 |
| Silicified Microcrystalline Cellulose | 89.0 | 104.0 |
| Silicon Dioxide | 2.0 | 2.0 |
| Mg-Stearate | 4.0 | 4.0 |
| Tablet Weight | 223 mg | 226 mg |

These 30 mg buspirone HCL test tablets, designed respectively for use as 24 hour and 12 hour extended release medicaments, were compared to a commercially available 15 mg buspirone HCL tablet (Buspar). To compensate for their lower drug content, the Buspar tablets were administered twice, at 0 and 12 hours, compared to the single administrations of the test tablets.

The three types of tablets were administered to a total of 16 to 18 subjects in a randomized, open-label, three treatment crossover program. The test results (with the commercial Buspar tablet, denominated as "BMS") were then graphed as FIG. 1 to show the mean plasma level of buspirone over time.

Through the suppression of peak height and the broadened base of the stronger test medicaments, the plots of FIG. 1 indicate the substantial prolongation of release and enhanced absorption of buspirone from complexes with anionic exchange polymer. The degree to which the complexes of this invention extend and monitor release is emphasized by the fact that, even after a repeat dosage with the conventional tablet after 12 hours, the buspirone plasma level of the conventional tablets drops below that of both types of the complex test tablets within about 6 and 9 hours, respectively.

Figure 2:
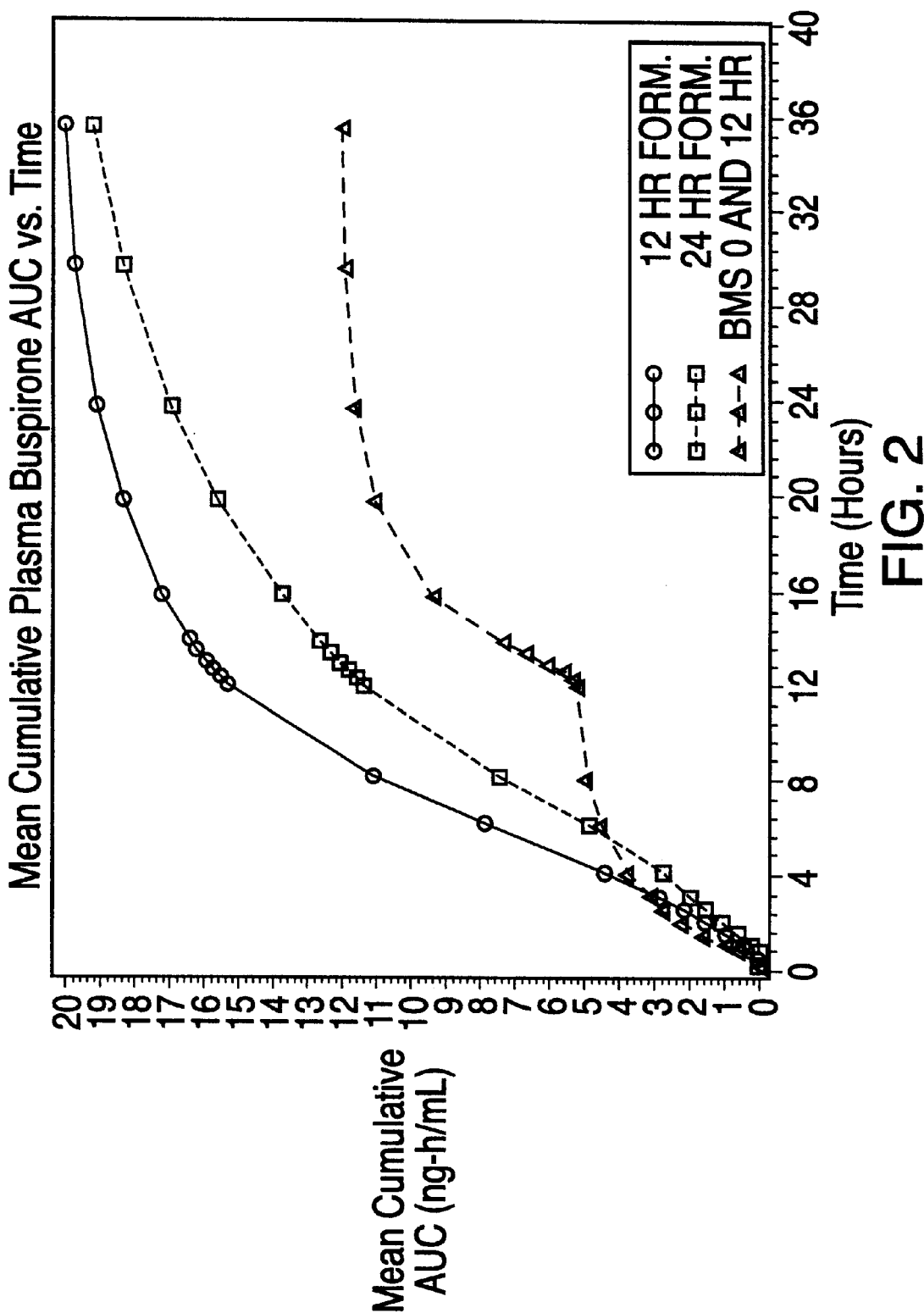
FIG. 2 is a graphic depiction of the comparative results obtained for mean cumulative plasma bioavailability levels of buspirone in Example 3.

The results of this program were then graphed to show the mean commutative plasma bioavailability of buspirone over time. These plots are set forth in FIG. 2.

These results are particularly surprising. It has frequently been reported that controlled/extended release forms of drugs subject to metabolic degradation show a reduced systemic availability compared to immediate release drug forms. As shown by these comparative plots, however, both of the prolonged release complex forms of buspirone exhibit substantially improved plasma bioavailabilities compared to the commercial, immediate release form.

To confirm this finding, the foregoing analysis was repeated for 1-PP, the major metabolite of buspirone. The results were then graphed as FIG. 3.

These graphic results confirm the prior conclusions. Despite the relatively lesser time of exposure of the non-complexed, commercial form of buspirone within the gastrointestinal tract, the bioavailability of 1-PP for the immediate release form equals or exceeds those obtained from the buspirone complex forms. This indicates the substantial protection which a complex of the present invention accords against the normal metabolic degradation of buspirone.

The foregoing examples are illustrative of the present invention. The scope of this invention is indicated by the appended claims, and all changes which come within the meaning and range of equivalency of these claims are intended to be embraced therein.

What is claimed is:

1. An oral dosage formulation for controlled release of a medicament comprising buspirone or a pharmaceutically acceptable salt thereof in intimate admixture with an anionic exchange polymer complexing agent.

2. The formulation of claim 1, wherein the salt comprises buspirone hydrochloride.

3. The formulation of claim 1, wherein the polymer comprises a hydrophilic anionic exchange polymer.

4. The formulation of claim 3, wherein the polymer comprises an anionic copolymer of methyl acrylic acid and ethyl acrylate.

5. The formulation of claim 4, wherein the salt comprises buspirone hydrchloride.

6. The formulation of claim 5, which additionally comprises a pharmaceutically acceptable viscosity enhancer.

7. The formulation of claim 6, wherein the viscosity enhancer is selected from the group consisting of hydroxypropylmethylcellulose and polyvinyl pyrolidine.

8. The formulation of claim 3, wherein the polymer comprises sodium carboxymethylcellulose.

9. The formulation of claim 8, wherein the salt comprises buspirone hydrochloride.

10. The formulation of claim 9, which additionally comprises a pharmaceutically acceptable viscosity enhancer.

11. The formulation of claim 10, wherein the viscosity enhancer is selected from the group consisting of hydroxypropylmethylcellulose and polyvinyl pyrolidine.

12. In a method for the palliative treatment of anxiety neurosis comprising orally administering an anxiolytically effective dose of drug to an anxious individual, the improvement wherein said drug comprises buspirone or a pharmaceutically accepted addition salt thereof combined with an anionic exchange polymer complexing agent.

13. The method of claim 12, wherein the salt comprises buspirone hydrochloride.

14. The method of claim 13, wherein the complexing agent comprises a copolymer of methyl acrylic acid and ethyl acrylate.

15. The method of claim 13, wherein the anionic complexing agent comprises sodium carboxylmethylcellulose.

* * * * *